(12) United States Patent
Mitchell et al.

(10) Patent No.: US 7,049,092 B1
(45) Date of Patent: May 23, 2006

(54) HORMONE-SENSITIVE LIPASE MEDIATED MALE INFERTILITY

(75) Inventors: Grant A. Mitchell, Saint-Leonard (CA); Shu Pei Wang, Dollard-des-Ormeaux (CA); Jacquetta Trasler, Dorval (CA); Louis Hermo, Montreal (CA)

(73) Assignee: Canadian Gene Cure Foundation, Vancouver (CA)

( * ) Notice: Subject to any disclaimer, the term of this patent is extended or adjusted under 35 U.S.C. 154(b) by 261 days.

(21) Appl. No.: 10/110,649

(22) PCT Filed: Oct. 13, 2000

(86) PCT No.: PCT/CA00/01228

§ 371 (c)(1),
(2), (4) Date: Jul. 9, 2002

(87) PCT Pub. No.: WO01/26664

PCT Pub. Date: Apr. 19, 2001

(30) Foreign Application Priority Data

Oct. 14, 1999 (CA) .................................. 2286451

(51) Int. Cl.
- *C12Q 1/34* (2006.01)
- *C12N 15/09* (2006.01)
- *C12N 9/20* (2006.01)
- *C07H 21/04* (2006.01)

(52) U.S. Cl. ..................... 435/18; 435/69.2; 435/198; 536/23.2

(58) Field of Classification Search ............... 435/69.1, 435/69.2, 198, 18; 536/23.2
See application file for complete search history.

(56) References Cited

U.S. PATENT DOCUMENTS 5,846,720 A 12/1998 Foulkes et al. ................ 435/6

FOREIGN PATENT DOCUMENTS

WO    WO 00/27388    5/2000
WO    WO 00/40569    7/2000

OTHER PUBLICATIONS

Holst et al. Genomics, 35, 441-447 (1996).*
Holst et al. [Genomics, 35, 441-447 (1996)].*
Stalfors et al. (1987), The Enzymes, vol. XVIII, pp. 147-177, Academic Press.*
Chinoy et al., "Amerlioration of fluoride toxicity in some accessory reproductive glands and spermatozoa of rat," *Fluoride* 28(2):75-86, 1995.
Holm et al., "Immunological evidence for the presence of hormone-sensitive lipase in rat tissues other than adipose tissue," *Biochem. Biophys. Res. Comm.* 148(1):99-105, Oct. 14, 1987.
Wang, et al., "Expression of Human Hormone-Sensitive Lipase (HSL) in Postmeiotic Germ Cells Confers Normal Fertility to HSL-Deficient Mice," *Endocrinology* 145(12):5688-5693 (2004).
Zambrowicz and Sands, "Knockouts Model the 100 Best-Selling Drugs—Will They Model the Next 100?" *Nature* 2:38-51 (Jan. 2003).
Zambrowicz et al., "Predicting drug efficacy: knockouts model pipeline drugs of the pharmaceutical industry," *Current Opinion in Pharm.* 3:563-570 (2003).

* cited by examiner

Primary Examiner—Tekchand Saidha
(74) Attorney, Agent, or Firm—Klarquist Sparkman, LLP

(57) ABSTRACT

In various aspects, the invention provides pharmacologic and genomic methods of inhibiting fertility in a male animal, such as human male contraception, involving the manipulation of the activity of hormone-sensitive lipase, including inhibiting the activity of a hormone-sensitive lipase in the animal. In another aspect, the invention discloses the use of hormone-sensitive lipase as a target in screening assays that may be used to identify compounds that modulate male fertility. In another aspect, the present invention identifies a condition of male infertility caused by hormone-sensitive lipase deficiency.

2 Claims, No Drawings

HORMONE-SENSITIVE LIPASE MEDIATED MALE INFERTILITY

CROSS REFERENCE TO RELATED APPLICATIONS

This is the National Stage of International Application No. PCT/CA/01228, filed Oct. 13, 2000, which was published in English under PCT Article 21(2), which in turn claims priority from Canadian Application No. 2,286,451, filed Oct. 14, 1999. Both applications are incorporated herein in their entirety.

FIELD OF THE INVENTION

The invention is in the field of pharmacologic and genomic methods of male contraception, involving the manipulation of the testicular activity of hormone-sensitive lipase.

BACKGROUND OF THE INVENTION

There is a continuing need for methods of modulating male fertility. For example, in humans, there is a need for alternatives to surgical approaches to male contraception such as castration and vasectomy. There is also a new and growing need for methods of inhibiting fertility in genetically modified organisms, as a means for preventing the dissemination of genetic modifications into wild-type populations.

Hormone-sensitive lipase (E.C. 3.1.1.3) has several substrates, all of which are fatty acyl esters. Hormone-sensitive lipase cleaves fatty acids from triacylglycerides and diacylglycerides at the 1- and 3-positions, cholesteryl esters and esters of retinoic acid and of steroid hormones. Hormone-sensitive lipase is active in adipose tissue, where it plays an important role in the release of fatty acids (Langin et al., 1996, *Proceeding of the Nutrition Society* 55:93). Hormone-sensitive lipase is also expressed in many non-adipose tissues, such as adrenal gland, pancreatic beta cells, macrophages and testicles (Holst et al., 1996, *Genomics* 35:441; Mulder et al., 1999, *Diabestes* 48:228; Reue et al., 1997, *Arterioscler Thromb Basic Biol* 17:3428; Blaise et al., 1999, *J. Biol. Chem* 274:9327).

The human hormone-sensitive lipase gene has been cloned (Langin et al., 1993, *Proc. Natl. Acad. Sci USA* 90:4897). Hormone-sensitive lipase is an amphiphilic 84 Kda protein with little homology to other mammalian lipases, containing three residues thought to be essential for serine protease activity (Ser 424, Asp 693 and His 723). In testes, hormone-sensitive lipase is expressed as a 130 KDa isoform, for which transcription begins in a specific upstream exon that is spliced to a site 22 base pairs upstream of the initiation methionine codon of nontesticular transcripts. The testicular hormone-sensitive lipase isoform therefore contains all of the sequence of nontesticular hormone-sensitive lipase plus an N-terminal extension encoded by the first (testes specific) exon. The testicular form of hormone-sensitive lipase is expressed at a specific phase of sperm development, in round and elongating spermatids.

A number of small molecule inhibitors of hormone-sensitive lipase are known, as shown in Table 1.

TABLE 1

| Inhibitors of hormone-sensitive lipase | |
|---|---|
| Inhibitor | IC50* |
| Diisopropylfluorophosphate (DFP) | 9 microM |
| HgCl$_2$ (mercuric chloride) | 11 microM |
| NaF (sodium fluoride) | 25 Mm |

*concentration producing 50% inhibition (Stralfors et al., 1987, The Enzymes, Vol. XVIII, p. 147–177, Academic Press)

SUMMARY OF THE INVENTION

In various aspects, the invention provides pharmacologic and genomic methods of inhibiting fertility in a male animal, such as human male contraception, involving the manipulation of the activity of hormone-sensitive lipase, including inhibiting the activity of a hormone-sensitive lipase in the animal. In the context of the invention, inhibiting the activity of hormone-sensitive lipase includes reducing the activity of hormone-sensitive lipase by suppression of enzymatic activity or suppression of transcription or translation of hormone-sensitive lipase. In one aspect, genomic manipulations may be used to affect the expression of hormone-sensitive lipase, or to affect the activity of the expressed enzyme. In another aspect, pharmaceuticals may be administered to modulate the activity of hormone-sensitive lipase. In some aspects of the invention, a testicular isoform of hormone-sensitive lipase may be the target of pharmacologic or genomic modulation. In some aspects, the invention provides methods of down-regulating testicular hormone-sensitive lipase to mediate male infertility by effecting the spermiogenesis phase of spermatogenesis. The method may for example comprise administering to the male animal an effective amount of a hormone-sensitive lipase inhibitor, which constitutes a use of a hormone-sensitive lipase inhibitor to inhibit fertility in a male animal.

In another aspect, the invention discloses the use of hormone-sensitive lipase as a target in screening assays that may be used to identify compounds that modulate male fertility. Such assays may be utilized to identify compounds that modulate expression of the hormone-sensitive lipase gene, or compounds that modulate the activity of the expressed enzyme. The testicular isoform of hormone-sensitive lipase may be used as the target in such assays. The use of a hormone-sensitive lipase in an assay to screen for a compound that inhibits male fertility may involve a method for identifying male fertility inhibitors comprising:
 a) providing a test compound;
 b) providing a hormone-sensitive lipase;
 c) providing a substrate for the hormone-sensitive lipase;
 d) assaying the activity of the hormone-sensitive lipase on the substrate in the presence of the test compound, to identify test compounds that inhibit the hormone-sensitive lipase.

The method may further comprise the step of assaying the compounds for inhibition of male fertility, for example by inhibiting spermatogenesis.

In another aspect, the present invention identifies a condition of male infertility caused by hormone-sensitive lipase deficiency. A screening method is therefore provided to provide information about testicular hormone-sensitive lipase activity in males. Such screening methods may be genomic or enzymatic, to screen respectively for expression or activity of hormone-sensitive lipase. Such screening methods may be used to identify individuals having reduced testicular hormone-sensitive lipase activity. Accordingly, a method of screening male patients, may comprise:
 a) identifying a male patient having reduced fertility;
 b) assaying the activity of a testicular hormone-sensitive lipase in the male patient.

DETAILED DESCRIPTION OF THE INVENTION

In one aspect of the invention, genomic manipulations may be used to affect the expression of hormone-sensitive lipase. Germ line transformation with a gene targeting vector may for example be used to disrupt expression of functional hormone-sensitive lipase, as described in Example 1. A wide variety of alternative genomic approaches are available to down-regulate the expression of functional hormone-sensitive lipase. For example, in alternative embodiments, transformation of cells with antisense constructs may be used to inhibit expression of hormone-sensitive lipase. Antisense constructs are nucleic acid molecules that may be transcribed to provide an antisense molecule that is substantially complementary to all or a portion of the mRNA encoding a hormone-sensitive lipase, so that expression of the antisense construct interferes with the expression of the hormone-sensitive lipase. SEQ ID NO:1 is for example a putative human mRNA encoding the testicular isoform of hormone-sensitive lipase, with the putative coding sequence shown in SEQ ID NO:1 and the protein sequence shown as SEQ ID NO: 2 (from Holst et al., 1995, GenBank Accession No. NM_005357; see also Holst et al., 1996, *Genomics* 35:441 and related GenBank Accession Nos. U40001 and U40002). In some embodiments, antisense constructs of the invention may therefore encode five or more contiguous nucleic acid residues substantially complimentary to a contiguous portion a nucleic acid sequence encoding a hormone-sensitive lipase, such as SEQ ID NO:1 or another mRNA encoding a mammalian hormone-sensitive lipase. In one aspect of the invention, antisense constructs may be provided that encode a nucleic acid that is complementary to a testis-specific portion of a hormone-sensitive lipase mRNA, such as the testis-specific exon of the human testicular isoform of hormone-sensitive lipase (Holst et al., 1996, *Genomics* 35:441).

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85:2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403–10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-value threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity of X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults word length (W) of 11, the BLOSUM62 scoring matrix (Henikoff and Henikoff, 1992, *Proc. Natl. Acad. Sci. USA* 89: 10915–10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison test of the sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO$_4$, 7% sodium dodecyl sulfate (SDS), 1 mM EDTA at 65EC, and washing in 0.2×SSC/0.1% SDS at 42EC (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65EC, and washing in 0.1×SSC/0.1% SDS at 68EC (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5EC lower than the thermal melting point for the specific sequence at a defined ionic strength and pH.

In alternative embodiments, the invention provides antisense molecules and ribozymes for exogenous administration to bind to, degrade and/or inhibit the translation of hormone-sensitive lipase mRNA. Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S.

Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the hormone-sensitive lipase mRNA to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as hormone-sensitive lipase inhibitors of the invention is disclosed in U.S. Pat. No. 5,932,435 (which is incorporated herein by reference).

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In another aspect, pharmaceuticals may be administered to modulate the activity of hormone-sensitive lipase. In this aspect of the invention, inhibitors of hormone-sensitive lipase may be selected from the group consisting of diisopropylfluorophosphate, mercuric chloride ($HgCl_2$) and sodium fluoride (NaF). In some aspects of the invention, a testicular isoform of hormone-sensitive lipase may be the target of pharmacologic or genomic modulation. For example, controlled-release formulations of hormone-sensitive lipase inhibitors may be administered to the testis or testicular region. In some aspects, the invention accordingly provides methods of down-regulating testicular hormone-sensitive lipase to mediate male infertility by affecting the spermiogenesis phase of spermatogenesis.

In another aspect, the invention discloses the use of hormone-sensitive lipase as a target in screening assays that may be used to identify compounds that modulate male fertility. In some embodiments, such an assay may comprise the steps of
   a) providing a test compound;
   b) providing a hormone-sensitive lipase;
   c) providing a substrate for the hormone-sensitive lipase;
   d) assaying the activity of the hormone-sensitive lipase on the substrate in the presence of the compound, to identify compounds that inhibit the hormone-sensitive lipase.

Such an assay may further comprise the step of assaying the compounds for spermatogenesis or spermiogenesis inhibiting activity. Such assays may be utilized to identify compounds that modulate expression of the hormone-sensitive lipase gene, or compounds that modulate the activity of the expressed enzyme. The testicular isoform of hormone-sensitive lipase may be used as the target in such assays.

In one embodiment, screening assays of the invention may comprise identifying compounds that modulate the cholesteryl esterase activity of hormone-sensitive lipase. For example, the neutral cholesteryl esterase activity of hormone-sensitive lipase may be assayed (Kraemer et al., 1993, *J. Lipid Res.* 34:663). In alternative embodiments, lipolysis may be measured (Susulic et al., 1995, *J. Biol. Chem.* 270:29483) with or without the addition of a lipolytic beta-3 adrenergic agonist, such as 10 μM CL316,243 (Wyeth-Ayerst Research Laboratories, Princeton, N.J., USA).

In another aspect, the present invention identifies a condition of male infertility caused by hormone-sensitive lipase deficiency. A screening method is therefore provided to provide information about testicular hormone-sensitive lipase activity in males. Such screening methods may be genomic or enzymatic, to screen respectively for expression or activity of hormone-sensitive lipase. Such methods are disclosed in Example 1. Such screening methods may be used to identify individuals having reduced testicular hormone-sensitive lipase activity.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLE 1

Murine transformation by blastocyst microinjection of a gene targeting vector was used to create chimeric mice having a functionally defective hormone-sensitive lipase allele. The mutant hormone-sensitive lipase allele lacked codons 2–172. The targeting vector was constructed from an AflII/BamHI subclone of a murine genomic hormone-sensitive lipase clone (Sztrolovics et al., 1997, *Mamm Genome* 8:86). In the mutant allele, 513 coding base pairs in exon 1 and 1,494 base pairs in intron 1 were replaced with a promoterless beta galactosidase gene inserted in frame with the hormone-sensitive lipase coding sequences, with a neomycin resistance cassette having a herpes simplex thymidine kinase promoter (pMC1Neo poly A, Stratagene).

Heterozygous F1 offspring of a male chimera with the mutant hormone-sensitive lipase allele and Balb/c females were crossed to produce mice for analysis. Germline transmission of the allele was obtained, and mice homozygous for the allele were produced.

Male hormone-sensitive-lipase-deficient mice having the defective hormone-sensitive lipase allele were completely infertile. Fertility was assessed by housing two month old males for 5 days with two CD1 females, then separating the females for 5 days before rebreeding. Females not becoming pregnant were shown to be fertile by subsequent mating with controls. Wild-type mice from the same litter had normal fertility. Mating occurred at a similar rate in the wild-type and hormone-sensitive-lipase-deficient mice, as indicated by the presence of mucus plugs in females that were housed with the mice. Seminal vesicles from the hormone-sensitive-lipase-deficient mice were of normal weight and histology, suggesting that these mice are not androgen deficient. Testicles from mutant mice weighed about half as much as those from normal mice, this is consistent with a lack of spermatozoa since spermatozoa comprise about half of normal testicular weight. Histology confirmed this, revealing an absence of spermatozoa in the seminal vesicles and epidiymis (i.e. azoospermia). Spermatogenesis was similar in hormone-sensitive-lipase-deficient and wild-type mice during the development of mitotic (spermatogonia) and meiotic (spermatocyte) germ cells. In postmeiotic development (spermiogenesis) marked abnormalities were noted in the germ cells of hormone-sensitive-lipase-deficient mice, including the presence of large cytoplasmic masses near the tubular lumen, multi-nucleated spermatids, some sharing a common acrosome, disruption of the normal orientation of the heads of late spermatids, and by stage VII of the seminiferous epithelial cycle a striking decrease in the number of late spermatids.

Southern blot analysis showed that the hormone-sensitive-lipase-deficient allele was present in the transformed mice. Northern analysis (Wang et al., 1993, *Mamm Genome* 4:382) using mouse cDNA probes from residues of 545–869 of the hormone-sensitive lipase gene showed that no normal hormone-sensitive lipase mRNA was expressed in these mice.

Cholesteryl esterase activity was undetectable in adipose tissue of mutant mice, consistent with a lack of functional hormone-sensitive lipase. Cholesteryl esterase activity was assayed as neutral cholesteryl esterase activity (Kraemer et al., 1993, *J. Lipid Res.* 34:663). Perigonadal fat pad adipocytes were isolated (Shillabeer and Lau, 1994, *J. Lipid Res.* 35:592) and lipolysis measured (Susulic et al., 1995, *J. Biol. Chem.* 270:29483) with or without the addition of 10 μM lipolytic beta-3 adrenergic agonist CL316,243 (Wyeth-Ayerst Research Laboratories, Princeton, N.J., USA). For each mixture, triglyceride concentration was assayed, the diameters of 200 adipocytes were measured following fixation in 4% glutaraldehyde and the mean adipocyte lipid content, content and surface area calculated.

Six-month-old hormone-sensitive-lipase-deficient mice were grossly normal and similar to wild-type littermates in weight and adipose tissue histology. Plasma triglyceride and nonesterified fatty acids were lower in hormone-sensitive-lipase-deficient males. The mean diameter of adipocytes isolated from perigonadal fat pads of six-month old mice was smaller in hormone-sensitive-lipase-deficient mice than in wild-type mice. When corrected for cell surface area, basal lipolysis in mutant adipocytes exceeded that of controls. Hormone-sensitive-lipase-deficient adipocytes lacked adrenergic responsiveness, in contrast to a 4- to 9-fold increase in wild-type adipocytes.

EXAMPLE 2

Therapeutic Formulations

In various embodiments, hormone-sensitive lipase inhibitors may be used therapeutically in formulations or medicaments to inhibit male fertility. The invention provides corresponding methods of medical treatment, in which a therapeutic dose of a hormone-sensitive lipase inhibitor is administered in a pharmacologically acceptable formulation. Accordingly, the invention also provides therapeutic compositions comprising an hormone-sensitive lipase inhibitor and a pharmacologically acceptable excipient or carrier. The therapeutic composition may be soluble in an aqueous solution at a physiologically acceptable pH.

The invention provides pharmaceutical compositions (medicaments) containing (comprising) hormone-sensitive lipase inhibitors. In one embodiment, such compositions include an hormone-sensitive lipase inhibitor in a therapeutically or prophylactically effective amount sufficient to alter, and preferably inhibit, spermiogenesis, and a pharmaceutically acceptable carrier.

A "therapeutically effective amount" refers to an amount effective, at dosages and for periods of time necessary, to achieve the desired therapeutic result, such as reduction or reversal of spermiogenesis, or reduction or inhibition male fertility. A therapeutically effective amount of hormone-sensitive lipase inhibitor may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of spermiogenesis or reducing male fertility. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the hormone-sensitive lipase inhibitors can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. hormone-sensitive lipase inhibitor) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an hormone-sensitive lipase inhibitor may be formulated with one or more additional compounds that enhance the solubility of the hormone-sensitive lipase inhibitor.

In accordance with another aspect of the invention, therapeutic compositions of the present invention, comprising a hormone-sensitive lipase inhibitor, may be provided in containers having labels that provide instructions for use of the hormone-sensitive lipase inhibitor to inhibit male fertility or inhibit spermiogenesis.

What is claimed is:

1. A method for identifying male fertility inhibitors comprising:
   a) providing a test compound;
   b) providing a testicular hormone-sensitive lipase having the amino acid sequence of SEQ ID NO: 2;
   c) providing a substrate for the hormone-sensitive lipase; and
   d) assaying the activity of the hormone-sensitive lipase on the substrate in the presence of the test compound, to identify test compounds that inhibit the hormone-sensitive lipase;
   wherein inhibition is indicative that the compound may be used to inhibit male fertility.

2. The method of claim 1, further comprising the step of assaying the compounds for spermatogenesis inhibiting activity.

* * * * *

SEQUENCE LISTING

```
<160> NUMBER OF SEQ ID NOS: 2

<210> SEQ ID NO 1
<211> LENGTH: 3804
<212> TYPE: RNA
<213> ORGANISM: HOMO SAPIENS
<220> FEATURE:
<221> NAME/KEY: CDS
<222> LOCATION: (278)..(3505)

<400> SEQUENCE: 1
cuucuuguaa gagagugcua ggcacauagc ccccuccuau uccuaauccu cccaccaaag      60
aaagaggcac agaguucauu acuuaguggg ggccagcugu gaucggccaa cugccagcug     120
ccuuaaaaag gaagaccagu gaugcuagga uggagugaaa cccaagagga agugccauca     180
ugaggaauca augagagauc ugugaagaga gagggcuggg ugggagccca gaaggauaga     240
accuggaaga ucaauaucuc ccgugaggga aauaaca aug gag cca ggu ucu aag      295
                                       Met Glu Pro Gly Ser Lys
                                         1               5 uca gug ucu agg uca gac ugg caa ccu gaa cca cac cag agg ccu aua       343
Ser Val Ser Arg Ser Asp Trp Gln Pro Glu Pro His Gln Arg Pro Ile
         10                  15                  20 acc ccg cua gag ccu ggg cca gaa aag aca ccc aua gcc cag cca gaa       391
```

-continued

```
                    Thr Pro Leu Glu Pro Gly Pro Glu Lys Thr Pro Ile Ala Gln Pro Glu
                                    25                  30                  35 ucg aag acu cug cag gga ucc aau acc caa cag aag ccu gcu uca aac          439
Ser Lys Thr Leu Gln Gly Ser Asn Thr Gln Gln Lys Pro Ala Ser Asn
 40                  45                  50 caa aga ccc cuc acc cag cag gag acc ccu gca caa cau gau gcu gaa          487
Gln Arg Pro Leu Thr Gln Gln Glu Thr Pro Ala Gln His Asp Ala Glu
 55                  60                  65                  70 ucc cag aag gaa ccu aga gcc caa caa aaa ucu gcu uca caa gag gaa          535
Ser Gln Lys Glu Pro Arg Ala Gln Gln Lys Ser Ala Ser Gln Glu Glu
                     75                  80                  85 uuu cuu gcc cca cag aag ccc gca cca cag caa uca ccu uac auc caa          583
Phe Leu Ala Pro Gln Lys Pro Ala Pro Gln Gln Ser Pro Tyr Ile Gln
                 90                  95                 100 agg gug cug cuc acu caa cag gaa gcu gcc ucc cag cag gga ccu ggg          631
Arg Val Leu Leu Thr Gln Gln Glu Ala Ala Ser Gln Gln Gly Pro Gly
             105                 110                 115 cua gga aaa gaa ucu aua acu caa cag gag cca gca uug aga caa aga          679
Leu Gly Lys Glu Ser Ile Thr Gln Gln Glu Pro Ala Leu Arg Gln Arg
         120                 125                 130 cau gua gcc cag cca ggg ccu ggg cca gga gag cca ccu cca gcu caa          727
His Val Ala Gln Pro Gly Pro Gly Pro Gly Glu Pro Pro Pro Ala Gln
135                 140                 145                 150 caa gaa gcu gaa uca aca ccu gcg gcc cag gcu aaa ccu gga gcc aaa          775
Gln Glu Ala Glu Ser Thr Pro Ala Ala Gln Ala Lys Pro Gly Ala Lys
                155                 160                 165 agg gag cca ucu gcc ccg acu gaa ucu aca ucc caa gag aca ccu gaa          823
Arg Glu Pro Ser Ala Pro Thr Glu Ser Thr Ser Gln Glu Thr Pro Glu
            170                 175                 180 cag uca gac aag caa aca acg cca guc cag gga gcc aaa ucc aag cag          871
Gln Ser Asp Lys Gln Thr Thr Pro Val Gln Gly Ala Lys Ser Lys Gln
        185                 190                 195 gga ucu uug aca gag cug gga uuu cua aca aaa cuu cag gaa cua ucc          919
Gly Ser Leu Thr Glu Leu Gly Phe Leu Thr Lys Leu Gln Glu Leu Ser
    200                 205                 210 aua cag cga uca gcc cua gag ugg aag gca cuu ucu gag ugg guc gca          967
Ile Gln Arg Ser Ala Leu Glu Trp Lys Ala Leu Ser Glu Trp Val Ala
215                 220                 225                 230 gau ucu gag uca gaa uca gau gug gga uca ucu uca gac aca gau ucu         1015
Asp Ser Glu Ser Glu Ser Asp Val Gly Ser Ser Ser Asp Thr Asp Ser
                235                 240                 245 cca gcc acg aug ggu gga aug gug gcc cag gga gug aag cua ggc uuc         1063
Pro Ala Thr Met Gly Gly Met Val Ala Gln Gly Val Lys Leu Gly Phe
            250                 255                 260 aaa gga aaa ucu ggu uau aaa gug aug uca gga uac agu ggg acg ucg         1111
Lys Gly Lys Ser Gly Tyr Lys Val Met Ser Gly Tyr Ser Gly Thr Ser
        265                 270                 275 cca cau gag aaa acc agu gcu cgg aau cac aga cac uac cag gau aca         1159
Pro His Glu Lys Thr Ser Ala Arg Asn His Arg His Tyr Gln Asp Thr
    280                 285                 290 gcc uca agg cuc auc cac aac aug gac cug cgc aca aug aca cag ucg         1207
Ala Ser Arg Leu Ile His Asn Met Asp Leu Arg Thr Met Thr Gln Ser
295                 300                 305                 310 cug gug acu cug gcg gag gac aac aua gcc uuc uuc ucg agc cag ggu         1255
Leu Val Thr Leu Ala Glu Asp Asn Ile Ala Phe Phe Ser Ser Gln Gly
                315                 320                 325 ccu ggg gaa acg gcc cag cgg cug uca ggc guu uuu gcc ggu gua cgg         1303
Pro Gly Glu Thr Ala Gln Arg Leu Ser Gly Val Phe Ala Gly Val Arg
            330                 335                 340
```

-continued

| | |
|---|---|
| gag cag gcg cug ggg cug gag ccg gcc cug ggc cgc cug cug ggu gug<br>Glu Gln Ala Leu Gly Leu Glu Pro Ala Leu Gly Arg Leu Leu Gly Val<br>      345                      350                          355 | 1351 |
| gcg cac cuc uuu gac cug gac cca gag aca ccg gcc aac ggg uac cgc<br>Ala His Leu Phe Asp Leu Asp Pro Glu Thr Pro Ala Asn Gly Tyr Arg<br>360                            365                        370 | 1399 |
| agc cua gug cac aca gcc cgc ugc ugc cug gcg cac cuc cug cac aaa<br>Ser Leu Val His Thr Ala Arg Cys Cys Leu Ala His Leu Leu His Lys<br>375                        380                        385                        390 | 1447 |
| ucc cgc uau gug gcc ucc aac cgc cgc agc auc uuc cgc acc agc<br>Ser Arg Tyr Val Ala Ser Asn Arg Arg Ser Ile Phe Phe Arg Thr Ser<br>                    395                        400                        405 | 1495 |
| cac aac cug gcc gag cug gag gcc uac cug gcu gcc cuc acc cag cuc<br>His Asn Leu Ala Glu Leu Glu Ala Tyr Leu Ala Ala Leu Thr Gln Leu<br>                410                        415                        420 | 1543 |
| cgc gcu cug guc uac uac gcc cag cgc cug cug guu acc aau cgg ccg<br>Arg Ala Leu Val Tyr Tyr Ala Gln Arg Leu Leu Val Thr Asn Arg Pro<br>425                        430                        435 | 1591 |
| ggg gua cuc uuc uuu gag ggc gac gag ggg cuc acc gcc gac uuc cuc<br>Gly Val Leu Phe Phe Glu Gly Asp Glu Gly Leu Thr Ala Asp Phe Leu<br>                440                        445                        450 | 1639 |
| cgg gag uau guc acg cug cau aag gga ugc uuc uau ggc cgc ugc cug<br>Arg Glu Tyr Val Thr Leu His Lys Gly Cys Phe Tyr Gly Arg Cys Leu<br>455                        460                        465                        470 | 1687 |
| ggc uuc cag uuc acg ccu gcc auc cgg cca uuc cug cag acc auc ucc<br>Gly Phe Gln Phe Thr Pro Ala Ile Arg Pro Phe Leu Gln Thr Ile Ser<br>                    475                        480                        485 | 1735 |
| auu ggg cug gug ucc uuc ggg gag cac uac aaa cgc aac gag aca ggc<br>Ile Gly Leu Val Ser Phe Gly Glu His Tyr Lys Arg Asn Glu Thr Gly<br>                490                        495                        500 | 1783 |
| cuc agu gug gcc gcc agc ucu cuc uuc acc agc ggc cgc uuu gcc auc<br>Leu Ser Val Ala Ala Ser Ser Leu Phe Thr Ser Gly Arg Phe Ala Ile<br>505                        510                        515 | 1831 |
| gac ccc gag cug cgu ggg gcu gag uuu gag cgg auc aca cag aac cug<br>Asp Pro Glu Leu Arg Gly Ala Glu Phe Glu Arg Ile Thr Gln Asn Leu<br>                520                        525                        530 | 1879 |
| gac gug cac uuc ugg aaa gcc uuc ugg aac auc acc gag aug gaa gug<br>Asp Val His Phe Trp Lys Ala Phe Trp Asn Ile Thr Glu Met Glu Val<br>535                        540                        545                        550 | 1927 |
| cua ucg ucu cug gcc aac aug gca ucg gcc acc gug agg gua agc cgc<br>Leu Ser Ser Leu Ala Asn Met Ala Ser Ala Thr Val Arg Val Ser Arg<br>                    555                        560                        565 | 1975 |
| cug cuc agc cug cca ccc gaa gcc uuu gag aug cca cug acu gcc gac<br>Leu Leu Ser Leu Pro Pro Glu Ala Phe Glu Met Pro Leu Thr Ala Asp<br>                    570                        575                        580 | 2023 |
| ccc acg cuc acg guc acc auc uca ccc cca cug gcc cac aca ggc ccu<br>Pro Thr Leu Thr Val Thr Ile Ser Pro Pro Leu Ala His Thr Gly Pro<br>585                        590                        595 | 2071 |
| ggg ccc guc cuc guc agg cuc auc ucc uau gac cug cgu gaa gga cag<br>Gly Pro Val Leu Val Arg Leu Ile Ser Tyr Asp Leu Arg Glu Gly Gln<br>                600                        605                        610 | 2119 |
| gac agu gag gag cuc agc agc cug aua aag ucc aac ggc caa cgg agc<br>Asp Ser Glu Glu Leu Ser Ser Leu Ile Lys Ser Asn Gly Gln Arg Ser<br>615                        620                        625                        630 | 2167 |
| cug gag cug ugg ccg cgc ccc cag cag gca ccc cgc ucg cgg ucc cug<br>Leu Glu Leu Trp Pro Arg Pro Gln Gln Ala Pro Arg Ser Arg Ser Leu<br>                    635                        640                        645 | 2215 |
| aua gug cac uuc cac ggc ggu ggc uuu gug gcc cag acc ucc aga ucc<br>Ile Val His Phe His Gly Gly Gly Phe Val Ala Gln Thr Ser Arg Ser<br>                650                        655                        660 | 2263 |

-continued

| | | |
|---|---|---|
| cac gag ccc uac cuc aag agc ugg gcc cag gag cug ggc gcc ccc auc<br>His Glu Pro Tyr Leu Lys Ser Trp Ala Gln Glu Leu Gly Ala Pro Ile<br>665 670 675 | | 2311 |
| auc ucc auc gac uac ucc cug gcc ccu gag gcc ccc uuc ccc cgu gcg<br>Ile Ser Ile Asp Tyr Ser Leu Ala Pro Glu Ala Pro Phe Pro Arg Ala<br>680 685 690 | | 2359 |
| cug gag gag ugc uuc uuc gcc uac ugc ugg gcc auc aag cac ugc gcc<br>Leu Glu Glu Cys Phe Phe Ala Tyr Cys Trp Ala Ile Lys His Cys Ala<br>695 700 705 710 | | 2407 |
| cuc cuu ggc uca aca ggg gaa cga auc ugc cuu gcg ggg gac agu gca<br>Leu Leu Gly Ser Thr Gly Glu Arg Ile Cys Leu Ala Gly Asp Ser Ala<br>715 720 725 | | 2455 |
| ggc ggg aac cuc ugc uuc acc gug gcu cuu cgg gca gca gcc uac ggg<br>Gly Gly Asn Leu Cys Phe Thr Val Ala Leu Arg Ala Ala Ala Tyr Gly<br>730 735 740 | | 2503 |
| gug cgg gug cca gau ggc auc aug gca gcc uac ccg gcc aca aug cug<br>Val Arg Val Pro Asp Gly Ile Met Ala Ala Tyr Pro Ala Thr Met Leu<br>745 750 755 | | 2551 |
| cag ccu gcc gcc ucu ccc ucc cgc cug cug agc cuc aug gac ccc uug<br>Gln Pro Ala Ala Ser Pro Ser Arg Leu Leu Ser Leu Met Asp Pro Leu<br>760 765 770 | | 2599 |
| cug ccc cuc agu gug cuc ucc aag ugu guc agc gcc uau gcu ggu gca<br>Leu Pro Leu Ser Val Leu Ser Lys Cys Val Ser Ala Tyr Ala Gly Ala<br>775 780 785 790 | | 2647 |
| aag acg gag gac cac ucc aac uca gac cag aaa gcc cuc ggc aug aug<br>Lys Thr Glu Asp His Ser Asn Ser Asp Gln Lys Ala Leu Gly Met Met<br>795 800 805 | | 2695 |
| ggg cug gug cgg cgg gac aca gcc cug cuc cuc cga gac uuc cgc cug<br>Gly Leu Val Arg Arg Asp Thr Ala Leu Leu Leu Arg Asp Phe Arg Leu<br>810 815 820 | | 2743 |
| ggu gcc ucc uca ugg cuc aac ucc uuc cug gag uua agu ggg cgc aag<br>Gly Ala Ser Ser Trp Leu Asn Ser Phe Leu Glu Leu Ser Gly Arg Lys<br>825 830 835 | | 2791 |
| ucc cag aag aug ucg gag ccc aua gca gag ccg aug cgc cgc agu gug<br>Ser Gln Lys Met Ser Glu Pro Ile Ala Glu Pro Met Arg Arg Ser Val<br>840 845 850 | | 2839 |
| ucu gaa gca gca cug gcc cag ccc cag ggc cca cug ggc acg gau ucc<br>Ser Glu Ala Ala Leu Ala Gln Pro Gln Gly Pro Leu Gly Thr Asp Ser<br>855 860 865 870 | | 2887 |
| cuc aag aac cug acc cug agg gac uug agc cug agg gga aac ucc gag<br>Leu Lys Asn Leu Thr Leu Arg Asp Leu Ser Leu Arg Gly Asn Ser Glu<br>875 880 885 | | 2935 |
| acg ucg ucg gac acc ccc gag aug ucg cug uca gcu gag aca cuu agc<br>Thr Ser Ser Asp Thr Pro Glu Met Ser Leu Ser Ala Glu Thr Leu Ser<br>890 895 900 | | 2983 |
| ccc ucc aca ccc ucc gau guc aac uuc uua uua cca ccu gag gau gca<br>Pro Ser Thr Pro Ser Asp Val Asn Phe Leu Leu Pro Pro Glu Asp Ala<br>905 910 915 | | 3031 |
| ggg gaa gag gcu gag gcc aaa aau gag cug agc ccc aug gac aga ggc<br>Gly Glu Glu Ala Glu Ala Lys Asn Glu Leu Ser Pro Met Asp Arg Gly<br>920 925 930 | | 3079 |
| cug ggc guc cgu gcc gcc uuc ccc gag ggu uuc cac ccc cga cgc ucc<br>Leu Gly Val Arg Ala Ala Phe Pro Glu Gly Phe His Pro Arg Arg Ser<br>935 940 945 950 | | 3127 |
| agc cag ggu gcc aca cag aug ccc cuc uac ucc uca ccc aua guc aag<br>Ser Gln Gly Ala Thr Gln Met Pro Leu Tyr Ser Ser Pro Ile Val Lys<br>955 960 965 | | 3175 |
| aac ccc uuc aug ucg ccg cug cug gca ccc gac agc aug cuc aag agc<br>Asn Pro Phe Met Ser Pro Leu Leu Ala Pro Asp Ser Met Leu Lys Ser | | 3223 |

```
                    970              975              980
cug cca ccu gug cac auc gug gcg ugc gcg cug gac ccc aug cug gac                3271
Leu Pro Pro Val His Ile Val Ala Cys Ala Leu Asp Pro Met Leu Asp
            985              990              995 gac ucg guc aug cuc gcg cgg cga cug cgc aac cug ggc cag ccg                    3316
Asp Ser Val Met Leu Ala Arg Arg Leu Arg Asn Leu Gly Gln Pro
    1000             1005             1010 gug acg cug cgc gug gug gag gac cug ccg cac ggc uuc cug acc                    3361
Val Thr Leu Arg Val Val Glu Asp Leu Pro His Gly Phe Leu Thr
    1015             1020             1025 cua gcg gcg cug ugc cgc gag acg cgc cag gcc gca gag cug ugc                    3406
Leu Ala Ala Leu Cys Arg Glu Thr Arg Gln Ala Ala Glu Leu Cys
    1030             1035             1040 gug gag cgc auc cgc cuc guc cuc acu ccu ccc gcc gga gcc ggg                    3451
Val Glu Arg Ile Arg Leu Val Leu Thr Pro Pro Ala Gly Ala Gly
    1045             1050             1055 ccg agc ggg gag acg ggg gcu gcg ggg gua gac ggg ggc ugc ggg                    3496
Pro Ser Gly Glu Thr Gly Ala Ala Gly Val Asp Gly Gly Cys Gly
    1060             1065             1070 ggg cga cac uaaaagccug uuguucccau cugcgccggc ucccgucaug                        3545
Gly Arg His
    1075 aaugccuucc gggccgggcg aaggggacg cgggcugugc uuacuuaagu cgggggugc                3605 aaggggcgg ggcgggggcc gaaagcugag acccucgcca cggggagggg gacgcgcaca              3665 cacaccgguc accgagacgg cuggaccugc acgccaccgc ugccuuuugc ugcugcugcu              3725 gcggcgaccg ccgcagggac ggggacuggc ccucccuugc aggucgguuu gguuuguugu              3785 aaauaaaagu auuuaauua                                                           3804

<210> SEQ ID NO 2
<211> LENGTH: 1076
<212> TYPE: PRT
<213> ORGANISM: HOMO SAPIENS

<400> SEQUENCE: 2

Met Glu Pro Gly Ser Lys Ser Val Ser Arg Ser Asp Trp Gln Pro Glu
1               5                   10                  15

Pro His Gln Arg Pro Ile Thr Pro Leu Glu Pro Gly Pro Glu Lys Thr
            20                  25                  30

Pro Ile Ala Gln Pro Glu Ser Lys Thr Leu Gln Gly Ser Asn Thr Gln
        35                  40                  45

Gln Lys Pro Ala Ser Asn Gln Arg Pro Leu Thr Gln Gln Glu Thr Pro
    50                  55                  60

Ala Gln His Asp Ala Glu Ser Gln Lys Glu Pro Arg Ala Gln Gln Lys
65                  70                  75                  80

Ser Ala Ser Gln Glu Glu Phe Leu Ala Pro Gln Lys Pro Ala Pro Gln
                85                  90                  95

Gln Ser Pro Tyr Ile Gln Arg Val Leu Leu Thr Gln Gln Glu Ala Ala
            100                 105                 110

Ser Gln Gln Gly Pro Gly Leu Gly Lys Glu Ser Ile Thr Gln Gln Glu
        115                 120                 125

Pro Ala Leu Arg Gln Arg His Val Ala Gln Pro Gly Pro Gly Pro Gly
    130                 135                 140

Glu Pro Pro Pro Ala Gln Gln Glu Ala Glu Ser Thr Pro Ala Ala Gln
145                 150                 155                 160

Ala Lys Pro Gly Ala Lys Arg Glu Pro Ser Ala Pro Thr Glu Ser Thr
```

```
                    165                 170                 175
Ser Gln Glu Thr Pro Glu Gln Ser Asp Lys Gln Thr Thr Pro Val Gln
            180                 185                 190
Gly Ala Lys Ser Lys Gln Gly Ser Leu Thr Glu Leu Gly Phe Leu Thr
        195                 200                 205
Lys Leu Gln Glu Leu Ser Ile Gln Arg Ser Ala Leu Glu Trp Lys Ala
    210                 215                 220
Leu Ser Glu Trp Val Ala Asp Ser Glu Ser Glu Ser Asp Val Gly Ser
225                 230                 235                 240
Ser Ser Asp Thr Asp Ser Pro Ala Thr Met Gly Gly Met Val Ala Gln
            245                 250                 255
Gly Val Lys Leu Gly Phe Lys Gly Lys Ser Gly Tyr Lys Val Met Ser
        260                 265                 270
Gly Tyr Ser Gly Thr Ser Pro His Glu Lys Thr Ser Ala Arg Asn His
        275                 280                 285
Arg His Tyr Gln Asp Thr Ala Ser Arg Leu Ile His Asn Met Asp Leu
    290                 295                 300
Arg Thr Met Thr Gln Ser Leu Val Thr Leu Ala Glu Asp Asn Ile Ala
305                 310                 315                 320
Phe Phe Ser Ser Gln Gly Pro Gly Glu Thr Ala Gln Arg Leu Ser Gly
            325                 330                 335
Val Phe Ala Gly Val Arg Glu Gln Ala Leu Gly Leu Glu Pro Ala Leu
            340                 345                 350
Gly Arg Leu Leu Gly Val Ala His Leu Phe Asp Leu Asp Pro Glu Thr
        355                 360                 365
Pro Ala Asn Gly Tyr Arg Ser Leu Val His Thr Ala Arg Cys Cys Leu
    370                 375                 380
Ala His Leu Leu His Lys Ser Arg Tyr Val Ala Ser Asn Arg Arg Ser
385                 390                 395                 400
Ile Phe Phe Arg Thr Ser His Asn Leu Ala Glu Leu Glu Ala Tyr Leu
            405                 410                 415
Ala Ala Leu Thr Gln Leu Arg Ala Leu Val Tyr Tyr Ala Gln Arg Leu
            420                 425                 430
Leu Val Thr Asn Arg Pro Gly Val Leu Phe Phe Glu Gly Asp Glu Gly
        435                 440                 445
Leu Thr Ala Asp Phe Leu Arg Glu Tyr Val Thr Leu His Lys Gly Cys
    450                 455                 460
Phe Tyr Gly Arg Cys Leu Gly Phe Gln Phe Thr Pro Ala Ile Arg Pro
465                 470                 475                 480
Phe Leu Gln Thr Ile Ser Ile Gly Leu Val Ser Phe Gly Glu His Tyr
            485                 490                 495
Lys Arg Asn Glu Thr Gly Leu Ser Val Ala Ala Ser Ser Leu Phe Thr
            500                 505                 510
Ser Gly Arg Phe Ala Ile Asp Pro Glu Leu Arg Gly Ala Glu Phe Glu
        515                 520                 525
Arg Ile Thr Gln Asn Leu Asp Val His Phe Trp Lys Ala Phe Trp Asn
    530                 535                 540
Ile Thr Glu Met Glu Val Leu Ser Ser Leu Ala Asn Met Ala Ser Ala
545                 550                 555                 560
Thr Val Arg Val Ser Arg Leu Leu Ser Leu Pro Pro Glu Ala Phe Glu
            565                 570                 575
Met Pro Leu Thr Ala Asp Pro Thr Leu Thr Val Thr Ile Ser Pro Pro
            580                 585                 590
```

```
Leu Ala His Thr Gly Pro Gly Pro Val Leu Val Arg Leu Ile Ser Tyr
        595                 600                 605

Asp Leu Arg Glu Gly Gln Asp Ser Glu Glu Leu Ser Ser Leu Ile Lys
        610                 615                 620

Ser Asn Gly Gln Arg Ser Leu Glu Leu Trp Pro Arg Pro Gln Gln Ala
625                 630                 635                 640

Pro Arg Ser Arg Ser Leu Ile Val His Phe His Gly Gly Phe Val
                645                 650                 655

Ala Gln Thr Ser Arg Ser His Glu Pro Tyr Leu Lys Ser Trp Ala Gln
                660                 665                 670

Glu Leu Gly Ala Pro Ile Ile Ser Ile Asp Tyr Ser Leu Ala Pro Glu
            675                 680                 685

Ala Pro Phe Pro Arg Ala Leu Glu Glu Cys Phe Phe Ala Tyr Cys Trp
        690                 695                 700

Ala Ile Lys His Cys Ala Leu Leu Gly Ser Thr Gly Glu Arg Ile Cys
705                 710                 715                 720

Leu Ala Gly Asp Ser Ala Gly Gly Asn Leu Cys Phe Thr Val Ala Leu
                725                 730                 735

Arg Ala Ala Ala Tyr Gly Val Arg Val Pro Asp Gly Ile Met Ala Ala
                740                 745                 750

Tyr Pro Ala Thr Met Leu Gln Pro Ala Ala Ser Pro Ser Arg Leu Leu
        755                 760                 765

Ser Leu Met Asp Pro Leu Leu Pro Leu Ser Val Leu Ser Lys Cys Val
        770                 775                 780

Ser Ala Tyr Ala Gly Ala Lys Thr Glu Asp His Ser Asn Ser Asp Gln
785                 790                 795                 800

Lys Ala Leu Gly Met Met Gly Leu Val Arg Arg Asp Thr Ala Leu Leu
                805                 810                 815

Leu Arg Asp Phe Arg Leu Gly Ala Ser Ser Trp Leu Asn Ser Phe Leu
                820                 825                 830

Glu Leu Ser Gly Arg Lys Ser Gln Lys Met Ser Glu Pro Ile Ala Glu
        835                 840                 845

Pro Met Arg Arg Ser Val Ser Glu Ala Ala Leu Ala Gln Pro Gln Gly
850                 855                 860

Pro Leu Gly Thr Asp Ser Leu Lys Asn Leu Thr Leu Arg Asp Leu Ser
865                 870                 875                 880

Leu Arg Gly Asn Ser Glu Thr Ser Ser Asp Thr Pro Glu Met Ser Leu
                885                 890                 895

Ser Ala Glu Thr Leu Ser Pro Ser Thr Pro Ser Asp Val Asn Phe Leu
                900                 905                 910

Leu Pro Pro Glu Asp Ala Gly Glu Glu Ala Glu Ala Lys Asn Glu Leu
        915                 920                 925

Ser Pro Met Asp Arg Gly Leu Gly Val Arg Ala Phe Pro Glu Gly
        930                 935                 940

Phe His Pro Arg Arg Ser Ser Gln Gly Ala Thr Gln Met Pro Leu Tyr
945                 950                 955                 960

Ser Ser Pro Ile Val Lys Asn Pro Phe Met Ser Pro Leu Leu Ala Pro
                965                 970                 975

Asp Ser Met Leu Lys Ser Leu Pro Pro Val His Ile Val Ala Cys Ala
                980                 985                 990

Leu Asp Pro Met Leu Asp Asp Ser  Val Met Leu Ala Arg  Arg Leu Arg
        995                 1000                1005
```

```
Asn Leu Gly Gln Pro Val Thr  Leu Arg Val Val Glu  Asp Leu Pro
    1010                1015             1020

His Gly Phe Leu Thr Leu Ala  Ala Leu Cys Arg Glu  Thr Arg Gln
    1025                1030             1035

Ala Ala Glu Leu Cys Val Glu  Arg Ile Arg Leu Val  Leu Thr Pro
    1040                1045             1050

Pro Ala Gly Ala Gly Pro Ser  Gly Glu Thr Gly Ala  Ala Gly Val
    1055                1060             1065

Asp Gly Gly Cys Gly Gly Arg  His
    1070                1075
```